United States Patent
Morgan et al.

(10) Patent No.: US 12,106,194 B1
(45) Date of Patent: Oct. 1, 2024

(54) OPTIMIZATION OF INVESTIGATOR AND SITE LOCATION IDENTIFICATION

(71) Applicant: IQVIA Inc., Parsippany, NJ (US)

(72) Inventors: Kristy Morgan, Chapel Hill, NC (US); Mark Boone Brown, Raleigh, NC (US); Natalia Balko, London (GB); April Lewis, Gulph Mills, PA (US); Lucas Glass, Devon, PA (US); Elizabeth Bodine, Havertown, PA (US); Lena Dyrved, Copenhagen (DK); Esther Van Hulten, Le Tremblay sur Mauldre (FR); Masha Kazantseva, Chapel Hill, NC (US)

(73) Assignee: IQVIA Inc., Parsippany, NJ (US)

( * ) Notice: Subject to any disclaimer, the term of this patent is extended or adjusted under 35 U.S.C. 154(b) by 97 days.

(21) Appl. No.: 17/532,478

(22) Filed: Nov. 22, 2021

Related U.S. Application Data

(63) Continuation of application No. 15/785,179, filed on Oct. 16, 2017, now Pat. No. 11,210,606.

(51) Int. Cl.
G06N 20/00 (2019.01)
G06N 5/022 (2023.01)

(52) U.S. Cl.
CPC ............. *G06N 20/00* (2019.01); *G06N 5/022* (2013.01)

(58) Field of Classification Search
CPC .............................. G06N 20/00; G06N 5/022
See application file for complete search history.

(56) References Cited

U.S. PATENT DOCUMENTS

| | | |
|---|---|---|
| 8,793,145 B2 | 7/2014 | Kahn et al. |
| 11,210,606 B1 | 12/2021 | Morgan et al. |
| 2006/0229916 A1* | 10/2006 | Michelson ............. G16H 10/20 707/999.1 |
| 2014/0222444 A1 | 8/2014 | Cerello et al. |
| 2017/0103190 A1* | 4/2017 | Abraham ............... G16H 50/30 |
| 2018/0082197 A1* | 3/2018 | Aravamudan .......... G06F 40/30 |

OTHER PUBLICATIONS

Data-Driven Feasibility: Utilizing data-driven insights for country and site selection could be the single largest facor in mitigating risks, Parexel, dated Jan. 2015, 1 page.

(Continued)

*Primary Examiner* — Kevin W Figueroa
(74) *Attorney, Agent, or Firm* — Fish & Richardson P.C.

(57) ABSTRACT

A computer-implemented method includes a machine learning system receiving distinct types of data associated with multiple individual entities. For each of the individual entities, the machine learning system determines a first attribute that indicates a predicted attribute of the entity based on analysis of the data. The machine learning system also determines a second attribute that indicates a predicted quality attribute of the entity, based on analysis of the data. An attribute weighting module of the machine learning system generates weight values for each of the first attribute and the second attribute of the entity. The machine learning system generates a data structure that identifies a set of entities from among the multiple individual entities, where entities of the set are ranked based on a tier indicator that corresponds to either the first attribute, the second attribute, or both.

23 Claims, 6 Drawing Sheets

(56) References Cited

OTHER PUBLICATIONS

ERT Real-Time Analytics: All your data. All in one place. Without all the spreadsheets, ERT, dated Sep. 6, 2017, 2 pages.
ERT Site Feasibility: Smarter Site Selection Leveraging Historical Performance Data. ERT, dated Apr. 7, 2017, 15 pages.
ERT Site Feasibility: Smarter Site Selection Leveraging Historical Performance Data. ERT, dated Jan. 30, 2017, 2 pages.
GoBalto launches study startup solution Select, CenterWatch News Online: News and views on the clinical trials industry, dated Mar. 31, 2016, 2 pages.
Open sites on time and meet enrollment targets, goBalto Select, dated Jan. 29, 2016, 2 pages.

\* cited by examiner

OPTIMIZATION OF INVESTIGATOR AND SITE LOCATION IDENTIFICATION

CROSS REFERENCE TO RELATED APPLICATIONS

This application is a Continuation of U.S. application Ser. No. 15/785,179, filed Oct. 16, 2017, the disclosure of which is incorporated herein by reference.

FIELD

This specification relates to processes for optimizing and enhancing identification of investigators and site locations for conducting particular programs.

BACKGROUND

As part of the health care process, physicians or other medical care providers may perform clinical trials, programs, and other activities to evaluate the efficacy of a particular pharmaceutical drug or other medical treatment option. The use of health-related trial programs can help to identify treatment options for improving overall patient health and reducing health system costs. For the purposes of gaining approval of particular treatment option, a clinical trial or program can be a research study that prospectively assigns human participants/subjects or groups of human subjects to one or more health-related interventions to evaluate the effects on health outcomes.

The effectiveness of a trial can depend on the experience level, specialty and expertise, or physical assets of particular investigators (e.g., physicians, academic scholars, or industry professionals) or geographic site locations that are selected to host, perform, or otherwise conduct the study. An investigator(s), a geographic site location(s), or the investigator(s) and the site location(s) can form an entity (or multiple entities) that is evaluated and assessed to determine the entity's predicted likelihood of successfully conducting the clinical trial.

Current solutions for evaluating entities consolidate input data manually and are heavily dependent upon data exports from disparate computer systems and data feeds. These solutions prioritize investigators and site locations (e.g., entities) based on factors identified by human users, and tend to focus on a discrete set of variables and/or single data points. Moreover, current solutions are dependent upon user defined weightings for various factors that are used to evaluate entity performance and these weightings can be improperly biased by prior experience or client input.

SUMMARY

This specification describes use of machine learning and predictive analytics to generate a listing of entities that are tiered and ranked based on their predicted ability to successfully perform a trial program. Systems and processes are described for receiving a broad set of data inputs and for executing an end-to-end automated entity identification solution to generate a data structure that identifies the entities their respective tier indicators. This entity identification solution can be used to prioritize entities (e.g., investigators, site locations, or both) for clinical trial or other program consideration. The entity identification solution prioritizes entities based on use of machine learning analytics on data inputs about prior unique study characteristics as well as information about clinical trial phases and target patient populations.

One aspect of the subject matter described in this specification can be embodied in a computer-implemented method for implementation using a computing system that includes a machine learning system configured to execute at least one predictive analytics model to identify particular entities from among multiple entities. The method includes, receiving, at the machine learning system, a plurality of distinct types of data, the data being associated with each entity of the multiple entities, wherein each entity comprises at least one of: i) an investigator that is associated with a program, or ii) a geographic location for a site adapted to host individuals that perform activities of the program;

For each entity of the multiple entities, the method includes, determining, by the machine learning system and based on analysis of the data, a first attribute that indicates a predicted assessment of the entity's ability to perform the activities of the program; and determining, by the machine learning system and based on analysis of the data, a second attribute that indicates a predicted assessment of the entity's ability to comply with protocols of the program. The method also includes, generating, by an attribute weighting module of the machine learning system, weight values for each of the first attribute and the second attribute of the entity; and generating, by the machine learning system and based on the weight values, a data structure that identifies a set of entities from among the multiple entities, where entities of the set are ranked based on a tier indicator that corresponds to at least one of the first attribute or the second attribute.

These and other implementations can each optionally include one or more of the following features. For example, in some implementations, generating the data structure includes: generating, by the attribute weighting module, weight values for a subset of data included in the plurality of distinct types of data; ranking, by the machine learning system, entities included in the set of entities based on analysis of the weight values for each of the first attribute, the second attribute, and the subset of data; and generating the data structure that identifies the set of entities from among the multiple entities, where entities of the set are ranked based on respective tier indicators that corresponding to each of the first attribute, the second attribute, and the subset of data.

In some implementations generating the weight values comprises at least one of: analyzing performance data used to determine the first attribute and generating the weight values for the first attribute based in part on the analyzed performance data, the first attribute being at least a performance attribute; or analyzing participation data used to determine the first attribute and generating the weight values for the first attribute based in part on the analyzed participation data, the first attribute being at least a participation attribute.

In some implementations, generating the weight values for the second attribute includes: analyzing quality data used to determine the second attribute and generating the weight values for the second attribute based in part on the analyzed quality data, the second attribute being a quality attribute, wherein the weight values include a weight for respective quality factors included in the analyzed quality data, and where that respective quality factors are each relevant to assessing the entity's ability to comply with protocols of the program.

In some implementations, the weight values for the first attribute comprises at least one of: i) a weight for respective performance factors included in the analyzed performance data for the entity, where that respective performance factors are each relevant to predicting the attribute of the entity; or ii) a weight for respective participation factors included in the analyzed data relating to the participation attribute of the entity, where that respective participation factors are each relevant to assessing the entity's ability to perform the activities of the program.

In some implementations, determining the first attribute comprises: executing a performance predictive analytics model of the machine learning system to analyze historical performance data for the entity and that is included in the received data; generating, by the performance predictive analytics model, a performance parameter for the entity using the analyzed historical performance data, the performance parameter corresponding to the predicted assessment of the entity's ability to perform the activities of the program; and determining the first attribute based in part on the performance parameter.

In some implementations, determining the first attribute further includes: executing a participation predictive analytics model of the machine learning system to analyze historical participation data for the entity and that is included in the received data; generating, by the participation predictive analytics model, a participation parameter for the entity using the analyzed historical participation data, the participation parameter corresponding to the predicted assessment of the entity's ability to perform the activities of the program; and determining the first attribute based in part on the participation parameter.

In some implementations, determining the second attribute includes: executing a quality predictive analytics model of the machine learning system to analyze historical quality data for the entity and that is included in the received data; generating, by the quality predictive analytics model, a quality parameter for the entity using the analyzed historical quality data, the quality parameter corresponding to the predicted assessment of the entity's ability to comply with protocols of the program; and determining the second attribute based in part on the quality parameter.

In some implementations, the data structure defines a first listing for ranking each entity in the set of entities, and the method further comprises: generating, by the machine learning system, a second data structure that defines a second listing for ranking each entity in the set of entities, wherein the second data structure is generated based in part on the first listing and analysis of real-world data produced when at least one entity identified in the first listing performs the activities of the program.

Another aspect of the subject matter described in this specification can be embodied in a computer-implemented method for implementation using a computing system that includes a machine learning system configured to execute at least one predictive analytics model to identify particular entities from among multiple entities. The method includes receiving, at the machine learning system, a plurality of distinct types of data, the data being associated with each entity of the multiple entities, wherein each entity comprises at least one of: i) an investigator that is associated with a program, or ii) a geographic location for a site adapted to host individuals that perform activities of the program.

For each entity of the multiple entities, the method includes determining, by the machine learning system and based on analysis of the data, one or more scoring parameters for evaluating the entity's ability to perform the activities of the program. The method also includes, generating, by an attribute weighting module of the machine learning system, a respective weight value for each scoring parameter of the one or more scoring parameters; and generating, by the machine learning system and based on the respective weight value, a data structure that identifies a set of entities from among the multiple entities, where entities of the set are ranked based on a tier indicator that corresponds to at least one scoring parameter of the one or more scoring parameters.

Other implementations of this and other aspects include corresponding systems, apparatus, and computer programs, configured to perform the actions of the methods, encoded on computer storage devices. A computing system of one or more computers or hardware circuits can be so configured by virtue of software, firmware, hardware, or a combination of them installed on the system that in operation cause the system to perform the actions. One or more computer programs can be so configured by virtue of having instructions that, when executed by data processing apparatus, cause the apparatus to perform the actions.

The subject matter described in this specification can be implemented to realize one or more of the following advantages. The described subject matter may enable efficient and enhanced identification of entities or entity pairs that include at least one investigator and at least one site location for conducting particular activities or programs. A computing system uses data analysis modules to efficiently identify particular entities and geographic site locations where the entities can perform certain clinical activities relating to treatment programs for improving or enhancing medical treatment processes for different patient groups.

The described teachings enable use of predictive analytics to generate data structures that identify top tier investigators and site locations that have a strong likelihood of successfully performing the treatment programs. Such analytical processes enable computations for entity identification including individual entity scoring and ranking to be performed rapidly and efficiently. For example, the use of certain algorithms causes predictive models to learn optimal, or more efficient, entity identification processes which results in enhanced computational efficiency of processors of the computing system.

Such enhanced efficiency results in reduced processor utilization and memory access operations data processing operations for entity ranking and identification. Hence, system throughput is increased thereby leading to more efficient processor and memory utilization, which is an improvement to the computer system.

The details of one or more implementations of the subject matter described in this specification are set forth in the accompanying drawings and the description below. Other potential features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

Figure 1:
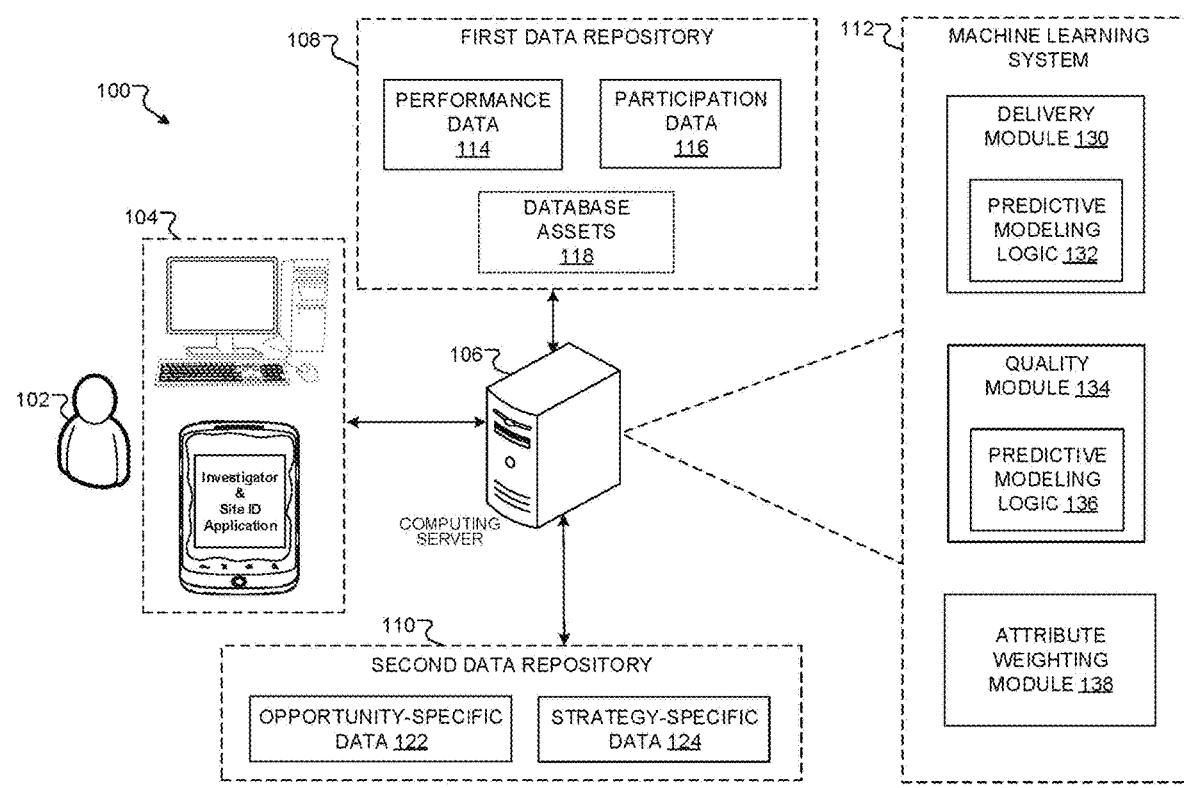
FIG. 1 shows a block diagram of a computing system for optimization of entity identification.

As part of the health care process, physicians or other medical care providers may perform trials program and other activities to evaluate the efficacy of a particular pharmaceutical drug or other medical treatment option. Conducting health-related clinical trials can help to identify medical treatment options for improving overall patient health and reducing health system costs. Physicians have interest in prescribing effective health care options for their patients and payers (e.g., insurance companies) have an interest in promoting, to their members, the use of health care options that are effective at mitigating on-going healthcare costs. Moreover, health care regulators as well as payers and providers are increasingly demanding information on the real-world uses and effectiveness of therapies which can provide a basis for performing real-world studies and programs.

There are numerous factors that have traditionally been used by the healthcare industry to identify and prioritize investigators and geographic site that can be used to conduct clinical trials. These factors typically include documented past performance on clinical trials, physician specialty, and customer input. Site identification teams can be formed to identify and drive the relative importance attributed to each factor that is used to rank investigators and site locations for various clinical trials.

In this context, systems and methods are described for optimizing identification of entities, e.g., investigators and geographic site locations, that are used to conduct clinical trials and other types of studies or programs. In general, the clinical trials and other programs can be used to determine treatment options that provide medical and health benefits to particular patient groups. In some implementations, programs include various types of studies, such as real-world prospective observational and pragmatic trials or reference programs.

The described teachings can be implemented to leverage sets of predictive algorithms that utilize machine learning processes across a broad array of data inputs. In other words, rather than rely on the current manual user defined ranking approach, this document describes computational processes for entity identification based on a comprehensive data analytics scoring approach. The data inputs include the traditional factors described above (e.g., past performance and physician specialty), but also introduces new factors such as historical protocol deviations, query rates, patient health claims and patient electronic medical record (EMR) data, prescription details, and available research publications by physicians.

The predictive algorithms are used to analyze the data inputs and, based on this analysis, predictive models can dynamically prioritize investigators and site locations for consideration on future clinical trials. Moreover, dynamic prioritization of investigators and site locations can include the on-going integration of new information for scoring and identifying entities. This on-going integration enables the predictive models to continuously learn and refine computing processes for identifying entities based on new or current data inputs. This document also describes the use of a model based approach to weighting various elements that contribute to dynamic prioritization of the investigators and site locations (e.g., entities). The described processes for entity identification can be tailored to study phases (including variations in appropriateness as well as interest by study phase) and particular patient populations to ensure that entities are prioritized by their predicted ability to enroll subjects and their predicted ability to produce high quality datasets for each aspect of a trial program.

FIG. 1 shows a block diagram of a computing system 100 for optimization of entity identification. System 100 can include multiple computers, computing servers, and other computing devices that each include processors and memory that stores compute logic or software instructions that are executable by the processors. In some implementations, multiple computers can form a cluster computing node, while multiple nodes can form node clusters. Cluster computing nodes and/or node clusters may be used to perform example computational and/or machine learning processes described herein.

System 100 includes a user device(s) 104, a computing server 106, a first data repository 108, a second data repository 110, and a machine learning system 112. Although depicted in FIG. 1 at least as a desktop computer console or smartphone, user device 104 can be any known computer system, such as a desktop computer, a laptop computer, a tablet device, a mobile device, a smartphone or any other related computing device that receives user input and that can transmit, transfer, or otherwise provide data and input commands to server 106.

In general, user device 104 is configured to receive user input from a human user 102 and system 100 can analyze or process the user input to cause server 106 to perform computational operations that are responsive to the user input. As discussed in more detail below, in some implementations, the user input may be a user command or query in which user 102 seeks a response from system 100, such as a listing of entities that are particularly suited for conducting high quality clinical trial programs.

A computing server 106 is configured to access each of data repository 108, data repository 110, and a machine learning system 112. In some implementations, machine learning system 112 is included within server 106 as a sub-system of hardware circuits that include at least one neural network represented by one or more processor microchips. In general, server 106 can include one or more processors, memory, and data storage devices that collectively form one or more computing systems of server 106. Processors of the computing systems process instructions for execution by server 106, including instructions stored in the memory or on the storage device to display graphical information for a graphical user interface (GUI) on an example display of, for example, user device 104.

Execution of the stored instructions can cause one or more of the actions described herein to be performed by server 106 (or machine learning system 112). In other implementations, multiple processors may be used, as appropriate, along with multiple memories and types of memory. For example, server 106 may be connected with multiple other computing devices, with each device (e.g., a server bank, groups of servers, modules, or a multi-processor system) performing portions of the actions or operations associated with the various processes or logical flows described in this specification.

First data repository 108 generally includes performance data 114, participation data 116, database assets 118, and attribute data 120. Performance data 114 can include a variety of datasets that have information indicative of an entity's past performance during a variety of different programs (e.g., certain clinical trials or other controlled programs involving primary data collection, including real-world and pragmatic programs). In some implementations, datasets of performance data 114 are analyzed to determine whether a particular entity is deemed to have successfully, or unsuccessfully, performed a particular trial program (described below). For example, data 114 can include information and other data about an entity's relative historical performance on certain objectives for different trial programs. The objectives can be Key Performance Indicators (KPIs) that are used to assess how well an entity performs with reference to a task that corresponds to a KPI.

Participation data 116 can include a variety of datasets that have information indicative of an entity's past participation in a variety of different programs (e.g., certain clinical trials or other controlled programs). System 100 can analyze data 116 to identify entities that are appropriately skilled to conduct, or participate in, trial studies and other programs based on a particular specialty of the entity and the experience level of the entity in conducting trial programs. In some implementations, participation data 116 is analyzed to determine whether a particular entity has the requisite experience, knowledge, processes, or physical assets (and other resources) that may contribute to an entity successfully performing a particular trial program.

For example, data 116 can include information and other data about an entity's historical participation cancer treatment programs, heart disease treatment programs, Alzheimer's treatment programs, non-health related programs, or other distinct types of trial programs. This historical data can be used to determine how well an entity might perform when conducting a future trial program based on the entity's participation in and experience level with certain past or historical trial other programs. In some implementations, data about an entity's experience or past participation in a first program (e.g., cancer treatment) can include factors that also contribute to an entity successfully performing a second program (e.g., Alzheimer's treatment) that is different than the first program.

Database assets 118 can include information about a variety of different patients, patient populations or patient groupings. In some implementations, assets of database 118 can be patient's electronic medical record (EMR), including EMR data inclusive of lab results, and other types of assets, such as claims data, prescription data, sales data for different treatment options, and lab data for different treatment options. A patient's EMR can provide a digital or electronic representation of the patient's hardcopy or paper medical chart and can include some or all information about the patient's medical history. In some implementations, database 118 is external to data repository 108 and server 106 is configured to access the database to retrieve and analyze patient data. Analysis of the patient data can indicate patient populations and other patient characteristics that can be used to identify entities.

Figure 2:
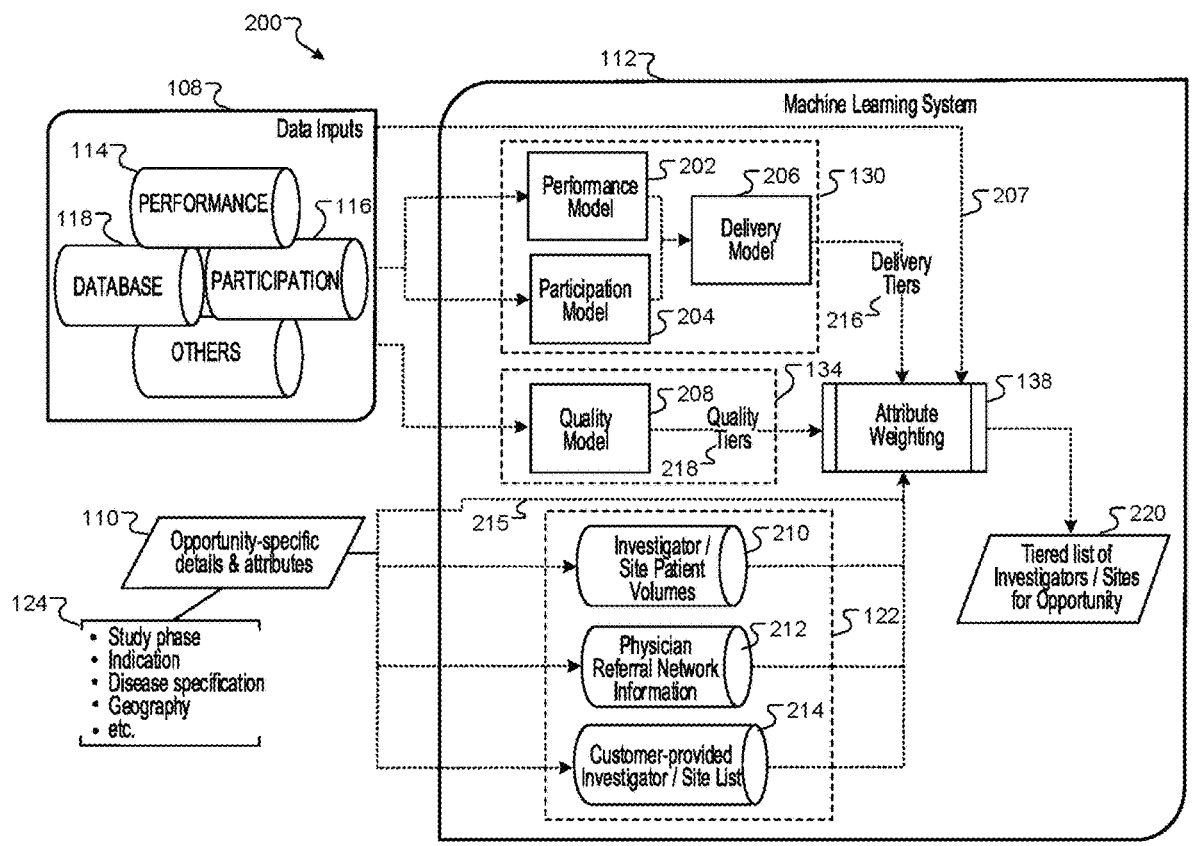
FIG. 2 shows a block diagram having computing modules of a machine learning system associated with the computing system of FIG. 1.

Second data repository 110 generally includes opportunity-specific data 122 and strategy-specific data 124. Data 122 can include information about opportunity-specific attributes, such as biosimilar experience of an entity, pediatric experience of an entity, spirometry capability of an entity, patient volumes and other patient that are tailored to particular study parameters, imaging quality of an entity, or other attributes that indicate unique or opportunity-specific attributes of an entity. As indicated by FIG. 2 (described below), in some implementations, opportunity-specific data 122 can be optionally received by machine learning system 112 for use in generating a listing of entities.

Strategy-specific data 124 can include information about strategy-specific attributes, such as entity partner status, experiences interacting with an entity from key leaders in an industry in which the entity operates, publication volumes associated with the entity, insights about the entity obtained from site management organizations (SMO), site network priority of the entity, and the extent to which an entity is categorized as experienced or inexperienced relative to the entity's experience level conducting various trial programs.

Machine learning (ML) system 112 includes a delivery module 130, a quality module 134, and an attribute weighting module 138. As used in this specification, the term "module" is intended to include, but is not limited to, one or more computers configured to execute one or more software programs that include program code that causes a processing unit(s) of the computing device to execute one or more functions. The term "computer" is intended to include any data processing or computing devices/systems, such as a desktop computer, a laptop computer, a mainframe computer, a personal digital assistant, a server, a handheld device, or any other device able to process data.

Delivery module 130 includes predictive modeling logic 132 for generating a listing of entities and their corresponding delivery tier (e.g, a delivery attribute), where the listing is generated based on an entity's predicted delivery performance. As described in more detail below, the delivery performance can be predicted by ML system 112 when module 130 executes computational processes associated with predictive modeling logic 132. In some implementations, delivery module 130 is used by ML system 112 to differentiate respective entities based on each entity's ability to perform a clinical, or other, trial program, combined with the appropriateness of the entity to conduct or participate in a particular trial program.

Quality module 134 includes predictive modeling logic 136 for generating a listing of entities and their corresponding quality tier (e.g, a quality attribute), where the listing is generated based on an entity's predicted quality risk. As described in more detail below, the quality risk can be predicted by ML system 112 when module 134 executes computational processes associated with predictive modeling logic 136. In some implementations, quality module 134 is used by ML system 112 to assess an entity's expected risk for quality issues based on the entity's past quality history. Quality module 134 can generate a single (or multiple) parameter values per entity to indicate the entity's expected quality risk.

ML system 112 uses attribute weighting module 138 to implement a model-based approach for analyzing and considering all available data inputs and attributes (e.g., data from repository 108, 110), as well as the tiered listings generated by each of modules 130 and 134. In some instances, inputs 207 correspond to certain data inputs that attribute weighting module 138 receives outside of the model results from 130 to 134. Weighting module 138 receives each of the various data inputs, analyzes the data inputs, and determines a weighting of each data input or attribute based on their relative importance. As described in more detail below, input weighting can be used together with the available data inputs and attributes to determine the appropriate final tiers for respective entities.

FIG. 2 shows a block diagram having computing modules that are associated with a computing system 200. The computing modules include program code for executing predictive models of ML system 112 of system 100. In some implementations, system 200 corresponds generally to ML system 112 and is a sub-system of system 100 described above with reference to FIG. 1. As shown, system 200 generally includes modules 130, 134, and 138 described above. System 200 further includes, a performance model 202, a participation model 204, and a delivery model 206 that are each associated with delivery module 130 as well as a quality model 208 that is associated with quality module 134.

Models 202, 204, 206, and 208 of system 200 each correspond to predictive analytics models that leverage machine learning techniques to automatically source and combine all available data to programmatically predict and prioritize the best entities for consideration on a particular trial program. For example, each model can be associated with a neural network. ML system 112 receives the data inputs and processes sets of inputs through layers of the neural network to compute inferences and generate predictions based on the computed inferences.

The neural network can be configured for one or more analytical learning processes that correspond to the respective inference or prediction capabilities of each model. In some implementations, the neural network of system 200 can be a single neural network (e.g., a neural network processor microchip) for each of models 202, 204, 206, and 208, or multiple respective neural networks where each of the respective neural networks correspond to a particular model 202, 204, 206, or 208.

System 200 and ML system 112 can generate control signals to cause at least one neural network processor of the system to execute programmed instructions or computing logic for performing the inference computations discussed above. Executing the computing logic can include using at least one algorithm to perform machine learning analytics. In some implementations, the algorithms include a single value decomposition algorithm or other related machine learning algorithms (e.g., maximum likelihood estimation algorithm).

Executing the computing logic enables each predictive model to determine or identify latent variables that identify relationships between data elements of data accessible from data repository 108, 110. In some implementations, such relationships are used to expand upon and further refine connections between data elements (e.g., performance data elements and participation data elements) that are used to generate inferences and predictions by the respective models. As used herein, latent variables, as opposed to observable variables, can be variables that are not directly observed but are rather inferred (e.g., through a predictive model) from other variables that are observed or directly analyzed and measured by models of ML system 112.

System 200 can be used to programmatically determine which data elements are predictive of future performance and use these data elements in the predictive modeling of entity rankings and entity prioritization. For example, leveraging this programmatic approach, system 200 is able to more accurately identify, relative to existing processes, the best and worst performing entities (e.g., the top ⅓ performing entities and the bottom ⅓ performing entities) from a delivery and quality perspective to ensure entities are differentiated and appropriately tiered for future trial programs.

Referring again to FIG. 2, data inputs (also referred to herein as input data, data elements, or input data elements) of data repository 108 are provided to, and received by, each of delivery module 130, quality module 134, and attribute weighting module 138. In particular, data inputs of data repository 108 are provided to, and received by, each of models 202, 204, 206, and 208. As noted above, delivery module 130 uses predictive modeling logic 132 to compute inferences for predicting an entity's performance in future clinical trials or other programs, while quality module 134 uses predictive modeling logic 136 to compute inferences for predicting an entity's quality risk in future clinical trials or other programs.

As described in more detail below, delivery module 130 uses models 202, 204, and 206 to generate respective delivery scores/parameters for rating each entity's relative historical performance on certain objective KPIs, while quality module 134 uses model 208 to generate respective quality scores/parameters for rating each entity's relative historical quality assessment for certain protocol deviations and other quality indicators. In some instances, delivery scores or parameters correspond to prediction data determined by ML system 112 based on analysis of data inputs from data repository 108, 110. The data inputs may represent historical data that can be used to infer or assess how an entity will perform prospectively when performing activities for a particular program.

For example, based on analysis of the data inputs, ML system 112 can generate prediction data that includes one or more scores or parameters (may be referred to as scoring parameters) for determining or assessing the entity's ability to perform the activities for conducting the program. The scoring parameters can be delivery scores that include numerical scores, e.g., that can range in value from 0.0-1.0, which are based on analysis of performance data 114, historical participation data 116, or other data inputs received from data repository 108. Additionally, the scoring parameters can be quality scores that include numerical scores, e.g., that can range in value from 0.0-1.0, which are based on analysis of quality data inputs received from data repository 108.

In some implementations, scoring/parameter data for rating each entity's historical performance on KPIs can include scoring parameters that are used to evaluate an entity's prospective ability to perform activities for conducting a particular clinical trial or other controlled program. Likewise, scoring/parameter data for rating each entity's historical quality assessments regarding deviations can include scoring parameters that are used to evaluate an entity's prospective ability to perform activities for conducting a particular clinical trial or other controlled program.

Performance model 202 is used by systems 100, 200 and delivery module 130 to predict an entity's expected performance based on the entity's observed clinical trial or other program experience. Model 202 can be configured to generate performance tier results by providing at least one parameter value for each entity. In some implementations, parameter values of the performance tier results can be combined with an example indication (described below) when delivery module 130 determines that an indication is relevant to determining a delivery tier of the entity.

Delivery module 130 can include software instructions or computing logic for data filtering operations. Execution of the software instructions causes data filters to be leveraged and applied to historical performance data received by module 130 and model 202 as data inputs from data repository 108, 110. In some implementations, the filtering logic analyzes (e.g., scans) and parses the data inputs and extracts, or filters for, performance data that: a) includes information about an entity's performance during particular study or trial phases (e.g., phases 2, 3, or 3b); b) includes study/trial status values; and c) includes records where investigator sites have been initiated/opened. Data inputs can be filtered to ensure that model 202 analyzes only those performance data elements that are more indicative of an entity's prospective performance in certain programs.

A broad series of data attributes and inputs can be analyzed and processed when inference computations are performed by model 202. For example, data attributes or performance data can include variables for particular indications of a program, where the indications are descriptive of a particular treatment option, or describe an effect a treatment option may have on a program participant. In some implementations, variables for a particular indication can include one or more of the following: i) a count of the number of studies on record within the indication; ii) an indicator for whether a program is an entity's first study in the indication; and iii) normalized enrollment rates (NER) for an entity's most recent study within the indication ("0" value NER for entity's with no prior studies).

Variables for a particular indication may further include one or more of the following: iv) median of normalized enrollment rates across all previous studies within the indication ("0" for entity's with no prior studies); v) a weighted average of a normalized enrollment rate across all previous studies within the indication, where more recent studies are weighted more heavily ("0" for entity's with no prior studies); vi) indicator for whether an entity's results in a more recent study were in the bottom 30% of enrollment rates for that study (a binary "0" or "1" indicator, e.g., "1" if in bottom 30%, or otherwise "0"); and vii) average of the bottom 30% indicators for the entity on all previous studies within the indication.

Data repositories 108, 110 can include data inputs and other data attributes that information about multiple indications (e.g., more than 300). Delivery module 130 can receive and analyze data inputs that have information about program study phases (e.g., phases 2, 3, or 3b). Module 130 can then use predictive modeling logic of model 202 to compute features for each of the multiple separate indications based on the analyzed information about the program study. Computed features can correspond to inference computations that are used to refine predictive functions of model 202. These predictive functions enable module 202 to generate prediction data for a multitude of features (e.g., over 2000) that correspond to the multiple indications.

Participation model 204 is used by systems 100, 200 and delivery module 130 to predict and/or identify indications for which it is appropriate that an entity participate in a program that may be associated with these indications. Additionally, model 204 is configured to predict or determine whether an entity is an appropriate candidate for a specific indication. These predictions and determinations can be based on the entity's observed program (e.g., clinical trial) experience, the entity's self-reported specialty information, or both. Model 204 generates a binary response variable ("0"/"1") to indicate whether an entity is an appropriate candidate for each indication or program. In some implementations, model 204 generates results variables for multiple respective combinations of indications and entities.

For example, model 204 can leverage entity self-reported specialties and documented program/trial experience to identify indications for which the entity can be identified as an appropriate option for a future program. In some implementations, analysis of participation data 116 indicates that an entity has documented experience in an indication that is inconsistent with their specialty (e.g., a pediatrician conducting an Alzheimer's trial). When this occurs an entity's association with a particular indication may still contribute to tier results for the entity.

Participation model 204 can analyze or assess participation data 116 that includes information about an entity's historical experience to determine appropriate indications for the entity. In some implementations, model 204 determines the indications based on one or more of the following: i) analysis of data records where investigator sites have been initiated/opened; and ii) analysis of data records where investigator sites have been selected, but not yet initiated/opened.

Participation model 204 can generate participation tier results by providing at least one parameter value for each entity. In some implementations, scores/parameter values of the participation tier results can be combined with a particular indication when delivery module 130 determines that an indication is relevant to determining a delivery tier of the entity. For an indication to be included in the participation results, the supporting dataset (e.g., participation data 116) should indicate that at least two investigator sites are initiated/opened for a given entity.

Participation model 204 can include at least two kinds of features, namely, 1) a count feature that represents a number of studies or programs an entity has conducted in each of a multitude of indications (e.g., more than 400 indications) and 2) a specialty feature that includes multiple binary indicators (or features) that show whether an entity is identified from participation data 116 as having a particular specialty. In some implementations, a number of indications that are available for data analysis operations of model 204 are dependent upon the experience and specialties identified by one or more entities.

Delivery model 206 includes predictive modeling logic for assessing and combining tier results data from performance model 202 and tier results data from participation model 204. In particular, delivery model 206 can be used to predict an entity's relative ability to perform or conduct a particular program, combined with the appropriateness for the entity to participate in programs that are associated with a certain identified indication(s). Hence, delivery model 206 is used by module 130 of ML system 112 to determine a delivery attribute/tier that indicates a predicted assessment of an entity's ability to perform activities of a program. For example, module 130 uses model 206 to generate numerical delivery tier values (e.g., scoring parameters) that can range in value from, for example, 1-12. In some implementations, tier values of 11 or 12 indicate certain entity's that have participation tier results, but that do not have performance tier results.

In some implementations, a tier value of "1" is the best tier result that can be assigned to an entity and indicates that an entity is predicted to exceed performance expectations when conducting a program. Conversely, a tier value of "10" is the worst tier result that can be assigned to an entity and indicates that an entity is predicted to not exceed minimum performance expectations when conducting a program. A tier value of "11" indicates that an entity has the appropriate specialty for an indication, that there is evidence of research experience that is relevant to the indication, but that there is no performance tier results data for the entity. A tier value of "12" indicates that an entity is appropriate for an indication, but that there is no available history of research experience for the entity.

Quality model 208 can generate at least one tier result value per entity based on analysis of data inputs received at module 134 from data repository 108, 110. For example, model 208 can receive data inputs having information about an entity's historical performance data, where the data includes program information indicating performance attributes and available protocol deviation history for each entity. In some implementations, model 208 is used to distinguish between entities that have high or low risks for quality issues during program execution based on the entity's observed site protocol deviations, subject-related protocol deviations, and a current quality assessment (QA) status.

For example, model 208 can execute computing logic for performing analysis on one or more of the following data elements of data repository 108, 110: a) QA status data; b) a number of site-level deviations (e.g., informed consent form (ICF), eligibility and entry criteria (EEC), investigational product (IP), serious adverse events (SAE), or source doc); c) a number of subjects with having subject-level deviations (e.g., ICF, EEC, IP, SAE, or source doc); d) total number of deviations including deviations identified as critical or major. In some implementations, this analysis enables model 208 to generate predictions about an entity's prospective quality risks during program execution.

Data inputs received at module 134 from data repository 108, 110 can include entity specific information regarding certain Key Risk Indicators (KRIs). In general, KRIs can be defined for different areas or aspects of a clinical trial or controlled program and may include a summary of results that reveal, amongst other things, protocol deviations in the program conduct across certain investigational sites. In some implementations, model 208 considers KRIs for each entity in order to support prediction of quality risks and determinations of quality attributes or scores. KRIs can include one or more of: protocol deviations, screen failure rates, query rates, SAEs, adverse events (AEs), or overdue action items.

Model 208 can receive data inputs about protocol deviations and QA status and perform machine learning analysis (including regression analysis) on the received inputs to determine relationships among variables of the received inputs. In some implementations, model 208 uses predictive modeling logic to compute inferences for predicting an entity's quality risk and generates quality tiers 218 (e.g., quality attributes) based on these computed inferences. Based on computed inferences, quality model 208 can be used by module 134 of ML system 112 to determine a quality attribute/tier corresponding to an entity's predicted quality risk. In some instances, the quality attribute/tier indicates a predicted assessment of an entity's ability to comply with protocols of a program when performing activities of the program. For example, module 134 uses quality model 208 to generate numerical quality tier values that can range in value from 1-12. In some implementations, a tier value of 12 is assigned to an entity that has no available data inputs that can be analyzed to determine a quality risk of the entity.

As used herein, protocols of a program can include requirements (e.g., quality requirements), program rules, or quality procedures/processes that should (or must) be adhered to when an entity conducts a program or clinical trial. In this context, references to protocol deviation(s) herein can include intentional or unintentional changes to, or non-compliance with, established program or clinical trial protocols. In some instances, a controlled program may have multiple subjects that undergo evaluation and some protocol deviations may have a significant effect on a program subject's rights, safety or welfare. Additionally, some protocol deviations may compromise overall integrity of data associated with the program data.

As described above, attribute weighting module 138 is used to implement a model-based approach for analyzing all available data inputs. In some implementations, data inputs include performance and participation attributes as well as the tiered result values generated by each of models 206 and 208. In some instances, tiered result values correspond to at least one of: i) a delivery tier/attribute, ii) a quality tier/attribute, or iii) respective scoring parameters for each entity in a set of entities. Attribute weighting module 138 can generate a respective weight value for each scoring parameter that can be determined by models 206, 208, where each scoring parameter may be associated with a particular entity.

Weighting module 138 receives each of these data inputs, analyzes the data inputs, and determines a weighting of each data input based on a predicted relative importance of the input. In some instances, data inputs received by module 138 can include entity patient volumes data 210, physician referral network data 212, and customer-provisioned entity listing data 214. Data 210, 212, and 214 each represent data attributes for opportunity-specific data 122 that can contribute to overall weighting determinations for an entity and that are provided directly to module 138 for determination of final entity weighting. Data 215 can correspond to other types of opportunity-specific data not delineated as data 210, 212, or 214. In other instances, data 215 corresponds to strategy-specific data 124 which can include a variety of data items, such as information about an entity's performance during certain study phases, experience with certain indications and disease specifications, or program activity in certain geographic regions. In some implementations, ML system 112 can be configured to perform weightings of data inputs of repository 108 without using, analyzing, or referencing opportunity-specific data 122 or information corresponding to data 215.

Weighting functions of module 138 are used along with the available data inputs and attributes to determine appropriate final tiers for respective entities that can be included in an example tiered entity listing 220. In some implementations, tiered entity listing 220 represents an example data structure generated by ML system 112 to identify sets of entities. In some implementations, entities of the set are scored or ranked based on analysis of received data inputs, where the data inputs include at least a tier indicator (e.g., a score/scoring parameter) for a delivery tier/attribute of the entity, a tier indicator for a quality tier/attribute of the entity, or both. For example, module 138 can determine respective weight values for the received data inputs and rank entities in a set based on analysis of the respective weight values. The data structure can include entities that are tiered based on the respective weight values that are assigned to data inputs of the entity.

Systems 100, 200 use data analytics to perform dynamic tiering of entities and to establish data-driven predictive models to compare and prioritize entities for consideration for future clinical trials. Models 202, 204, 206, and 208 generate predictions for delivery tier 216 and quality tier 218 by leveraging, for example, data inputs with information about an entity's historical performance and participation during past trials, an entity's self-reported specialty or area of expertise, and insights about an entity's quality issues and/or quality successes during past trials.

Data inputs of repository 108, 110 can be continually analyzed and incorporated into the inference computations of models 202, 204, 206, and 208. In general, the delivery and quality tiering models 206 and 208 produce at least one respective element for prioritization of entities, delivery tier 216 and quality tier 218. Delivery tier 216 is based on an entity's predicted delivery performance, while quality tier 218 is based on an entity's predicted quality risk.

In some implementations, systems 100, 200 implement automation logic for performing the tiering functions of models 202, 204, 206, and 208. Automation logic enables each model to be re-run automatically so that use of stale or outdated information for generating new predictions is substantially reduced.

As indicated above, ML system 112 is configured for dynamic prioritization of entities, which includes on-going integration of new information for scoring/ranking and identifying entities. On-going integration enables the predictive models of ML system 112 to continuously learn and refine computing processes for identifying entities based on new or current data inputs. In some implementations, the new or current data inputs are based on controlled programs, such as real-world prospective observational and pragmatic trials or reference programs.

For example, data structure 220 can define a first listing for ranking each entity in a set of entities, and ML system 112 can generate a second data structure 220 that defines a second listing for ranking each entity in the set of entities. The second data structure may be generated based at least in part on: i) the first listing and ii) analysis of real-world data produced when at least one entity identified in the first listing performs activities for conducting a program. In some implementations, real-world data that is produced when an entity conducts a program can include analysis factors that indicate an entity's current performance relative to certain KPIs or KRIs. The real-world data can also include quality risk indicators, such as information about an entity's compliance with protocol deviations and other program procedures when conducting the program.

In example embodiments, an initial listing (first listing) for ranking entities can be generated. The entities of the initial listing can be dynamically prioritized or re-prioritized when ML system 112 performs on-going integration of new information for use in scoring/ranking and identifying particular entities. For example, the new information can correspond to real-world performance, participation, and quality data which indicate the real-world attributes of how an entity conducts a current program. Dynamic prioritization of the initial listing can include ML system 112 analyzing the new information to generate at least one subsequent listing (second listing) to rank/re-rank entities using the real-world data.

Weighting module 138 can perform weighting of these new analysis factors. The weighting process may include determining or generating some weight/parameter value (e.g., ranging 0.0 to 1.0), where a value can be generated based on a certain KPI parameter (e.g., a scaled KPI score) or a KRI parameter (e.g., a scaled KRI score). In some implementations, the weight value is generated based on computations involving a scaled KPI/KRI score and an entity's tier value/score within the first listing. For example, computations can include multiplying the scaled KPI/KRI score with the entity's tier value, or performing other mathematical operations using the scaled score and the tier value.

As described above, each of models 202, 204, 206, and 208 is configured to differentiate predictions based upon study targeted patient population and trial program phase to ensure the ideal entity prioritization (e.g., entities are ranked and tiered) for each future clinical trial or program scenario. Moreover, identifying investigators/sites for conducting a future trial includes analysis of, and accounting for, numerous considerations. Hence, at least one aim of the described systems and processes is to identify and eventually activate entities that will enroll subjects on a trial program through to completion and provide high quality data, in support of the trial conduct.

Figure 3A:
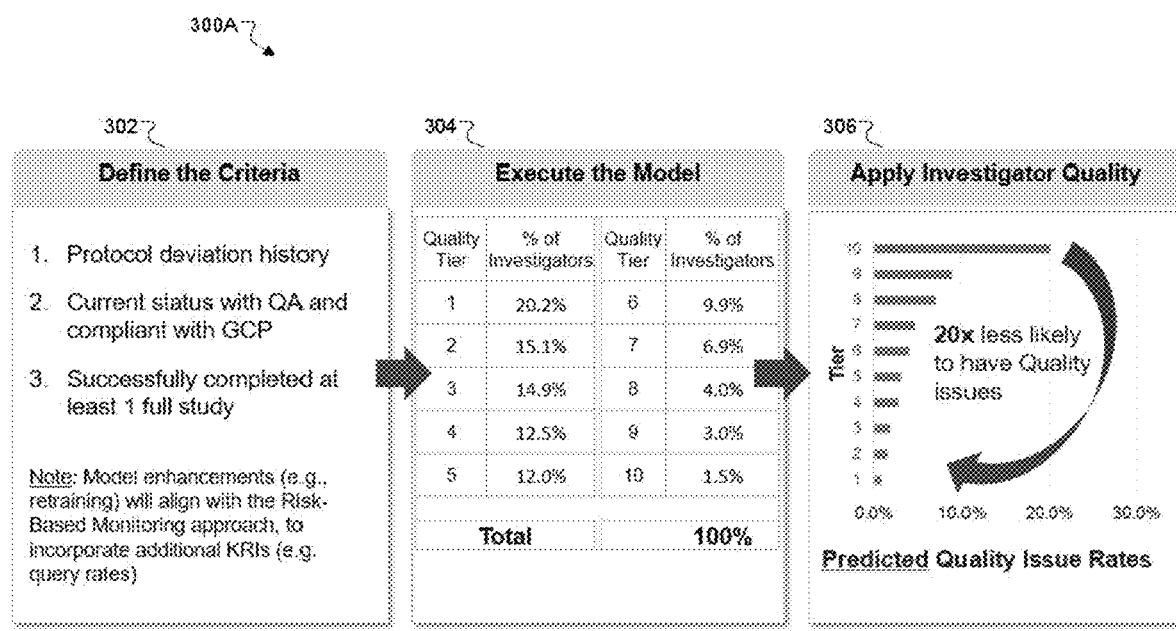
FIGS. 3A and 3B each show graphical data relating to optimization of entity identification.
Figure 3B:
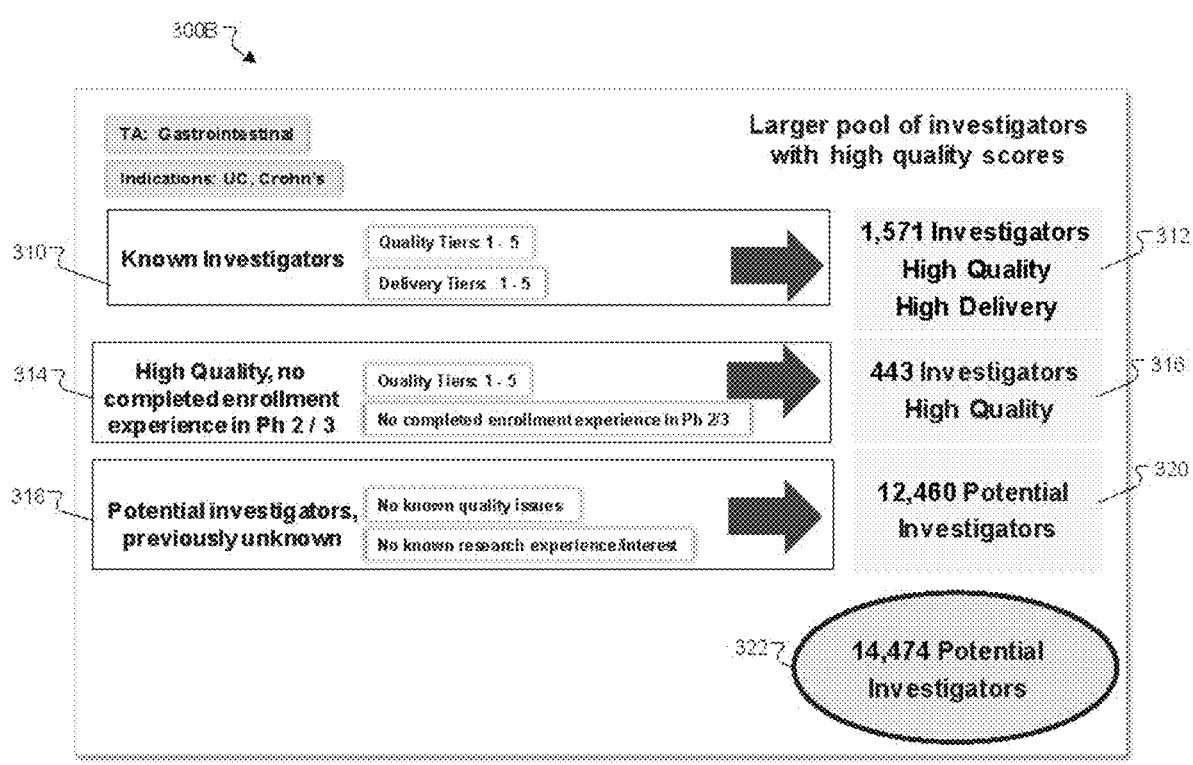

FIGS. 3A and 3B each show graphical data 300A and 300B relating to optimization of entity identification. Referring to FIG. 3A, graphical data 300A includes criteria 302, execution data 304, and quality data 306. Criteria 302 represents example criteria for evaluating an entity. Criteria 302 can include protocol deviation history, a current quality and compliance status, data about the number of prior studies that were completed by the entities, or a variety of other criteria relating to performance, participation, and quality attributes of an entity. Execution data 304 can correspond to an example data structure that is generated when quality model 208 of ML system 112 is executed and includes a listing of entities that are identified and listed in the data structure based on their quality tier. Quality data 306 indicates that entities associated with a good quality tier (e.g., 1) are 20% less likely to have a quality issue (e.g., a protocol deviation) relative to an entity that is assigned to a poor quality tier (e.g., 10).

Referring now to FIG. 3B, graphical data 300B includes a first data set 310 for identifying known investigators 312 that may have high quality and high delivery attributes when compared to the multiple other entities of all potential entities 322. Data 300B further includes a second data set 314 for identifying investigators 316 that may have high quality attributes when compared to the multiple other potential entities 322. However, investigators 316 may have no completed enrollment experience in phase 2 or 3 of clinical trials or other programs. Hence, no delivery attributes can be computed for these investigators.

Data 300B also includes a third data set 318 for identifying potential investigators 320 that were previously unknown and for which system 100 has no data indicating any known quality issues for computing quality attributes of the investigators 320 or any known research experience for computing delivery attributes of the investigators 320. As described herein, graphical data 300B indicates that, for potential entities 322, ML system 112 of system 100 can apply predictive algorithms to enhance geographic site selection and expand investigator pools. For example, using the described systems and methods, larger pools of investigators with high quality and/or delivery scores can be identified from among potential entities 322.

Figure 4:
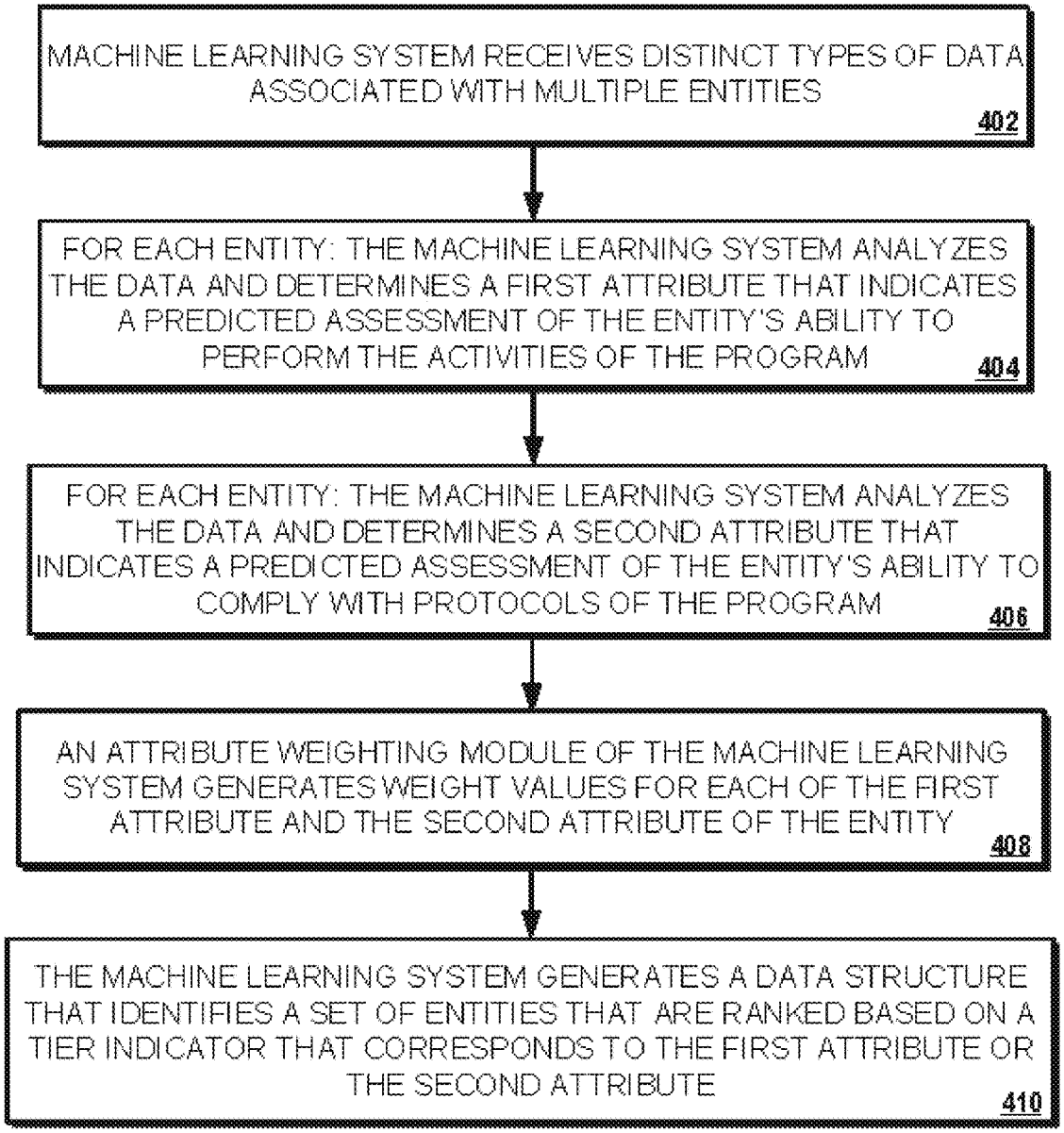
FIG. 4 shows a flow diagram of an example process for optimization of entity identification.

FIG. 4 shows a flow diagram of an example process 400 for optimization of entity identification. Process 400 can be implemented using system 100 and system 200 described above. Thus, descriptions of process 400 may reference one or more of the above-mentioned computing resources of systems 100 and 200. In some implementations, the described actions of process 400 can be enabled by computing logic or programmed instructions executable by one or more processors and memory of an example electronic device, such as server 106 or user device 104 described above.

Process 400 can correspond to a computer-implemented method that is implemented or executed using system 100, 200 and ML system 112 that is configured to execute at least one predictive analytics model to identify particular entities from among multiple entities. At block 402 of process 400, system 100 receives multiple distinct types of data inputs at ML system 112. The received data inputs can be associated with each of the multiple entities and can include information about: 1) an entity's performance attributes in past trial programs; 2) an entity's participation in past trial programs;

3) data elements received from a database having electronic medical data about human subjects that may be enrolled in a trial program.

At block 404, for each entity of the multiple entities, ML system 112 analyzes the received data inputs and, based on this analysis, determines a delivery tier that indicates a predicted attribute of the entity. For example, ML system 112 can use delivery model 206 to predict an entity's relative ability to perform or conduct a particular program, combined with the appropriateness for the entity to participate in programs that are associated with a certain identified indication(s). Model 206 can generate numerical delivery tier values that can range in value from, for example, 1-12.

At block 406, for each entity of the multiple entities, ML system 112 analyzes the received data inputs and, based on this analysis, determines a quality tier that indicates a predicted quality attribute of the entity. For example, quality model 208 can receive data inputs about protocol deviations and QA status. ML system 112 can use model 208 to execute learning analysis (including regression analysis), using the received inputs, to determine relationships among variables of the received inputs. Model 208 uses predictive modeling logic to compute inferences for predicting an entity's quality risk and generates quality tiers 218 based on these computed inferences.

At block 408, process 400 includes system 100 using attribute weighting module 138 of ML system 112 to generate weight values for each of the delivery tier and the quality tier of the entity as well as weight values for data elements that contribute to determining the respective delivery and quality tiers. In some implementations, generating the weight values for delivery tier 216 includes at least one of: i) analyzing data inputs used to determine delivery tier 216 and that relate to a performance attribute of an entity, and generating the weight values based in part on these analyzed data inputs; or ii) analyzing data inputs used to determine delivery tier 216 and that relate to a participation attribute of the entity, and generating the weight values based in part on these analyzed data inputs.

In some implementations, generating the weight values for quality tier 218 includes analyzing data inputs used to determine quality tier 218 and that relates to a quality attribute of an entity, and generating the weight values for quality tier 218 based in part on the analyzed data inputs. In some instances, the weight values include a weight for respective quality factors included in the analyzed data inputs that relate to the quality attribute, where that respective quality factors are each relevant to predicting the quality attribute of the entity.

At block 410 of process 400, ML system 112 generates an example data structure that identifies a set of entities that are ranked based on a tier indicator that corresponds to either the delivery tier, the quality tier, or both. In some implementations, generating the data structure includes attribute weighting module 138 determining respective weight values for a subset of data inputs (e.g., performance data, participation data, or other data) included in data repository 108, 110. Generating the data structure may further include ML system 112 ranking entities included in the set of entities based on analysis of the respective weight values for each of the delivery tier, the quality tier, and the subset of data. The data structure can include entities that are ranked based on their respective tier indicators that corresponding to each of the delivery tier, the quality tier, and the subset of data.

In some implementations, execution of process 400 includes ML system 112 using predictive analytics to generate inferences and predictions about a particular entities likelihood of successfully conducting a trial program. In some instances, the predictive analytics are implemented using the above described systems to enable efficient ranking and prioritization of the multiple entities. Such analytical learning processes enable computations for entity ranking and tiered prioritization to be performed rapidly and more efficiently relative to conventional systems.

Figure 5:
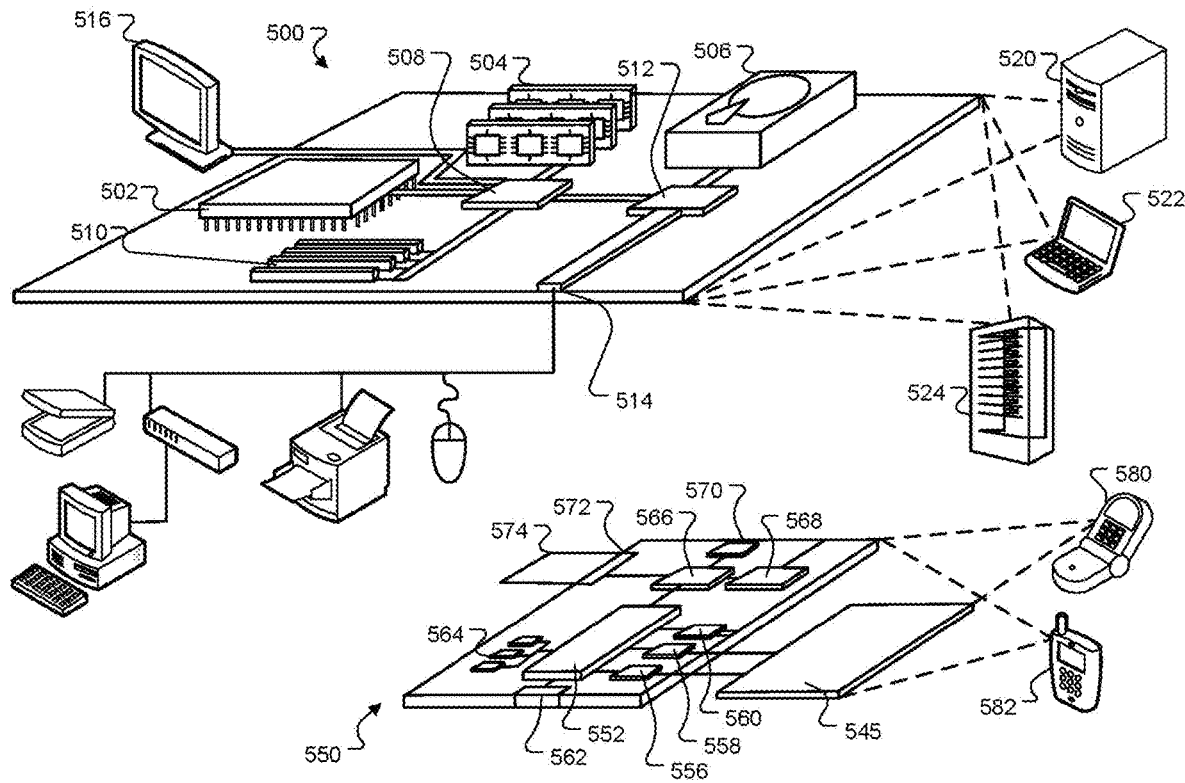
FIG. 5 shows a block diagram of a computing system that can be used in connection with computer-implemented methods described in this specification.

FIG. 5 is a block diagram of computing devices 500, 550 that may be used to implement the systems and methods described in this document, as either a client or as a server or plurality of servers. Computing device 500 is intended to represent various forms of digital computers, such as laptops, desktops, workstations, personal digital assistants, servers, blade servers, mainframes, and other appropriate computers. Computing device 550 is intended to represent various forms of mobile devices, such as personal digital assistants, cellular telephones, smartphones, smartwatches, head-worn devices, and other similar computing devices. The components shown here, their connections and relationships, and their functions, are meant to be exemplary only, and are not meant to limit implementations described and/or claimed in this document.

Computing device 500 includes a processor 502, memory 504, a storage device 506, a high-speed interface 508 connecting to memory 504 and high-speed expansion ports 510, and a low speed interface 512 connecting to low speed bus 514 and storage device 506. Each of the components 502, 504, 506, 508, 510, and 512, are interconnected using various busses, and may be mounted on a common motherboard or in other manners as appropriate. The processor 502 can process instructions for execution within the computing device 500, including instructions stored in the memory 504 or on the storage device 506 to display graphical information for a GUI on an external input/output device, such as display 516 coupled to high speed interface 508. In other implementations, multiple processors and/or multiple buses may be used, as appropriate, along with multiple memories and types of memory. Also, multiple computing devices 500 may be connected, with each device providing portions of the necessary operations, e.g., as a server bank, a group of blade servers, or a multi-processor system.

The memory 504 stores information within the computing device 500. In one implementation, the memory 504 is a computer-readable medium. In one implementation, the memory 504 is a volatile memory unit or units. In another implementation, the memory 504 is a non-volatile memory unit or units.

The storage device 506 is capable of providing mass storage for the computing device 500. In one implementation, the storage device 506 is a computer-readable medium. In various different implementations, the storage device 506 may be a floppy disk device, a hard disk device, an optical disk device, or a tape device, a flash memory or other similar solid state memory device, or an array of devices, including devices in a storage area network or other configurations. In one implementation, a computer program product is tangibly embodied in an information carrier. The computer program product contains instructions that, when executed, perform one or more methods, such as those described above. The information carrier is a computer- or machine-readable medium, such as the memory 504, the storage device 506, or memory on processor 502.

The high speed controller 508 manages bandwidth-intensive operations for the computing device 500, while the low speed controller 512 manages lower bandwidth-intensive operations. Such allocation of duties is exemplary only. In one implementation, the high-speed controller 508 is coupled to memory 504, display 516, e.g., through a graphics processor or accelerator, and to high-speed expansion ports 510, which may accept various expansion cards (not shown). In the implementation, low-speed controller 512 is coupled to storage device 506 and low-speed expansion port 514. The low-speed expansion port, which may include various communication ports, e.g., USB, Bluetooth, Ethernet, wireless Ethernet, may be coupled to one or more input/output devices, such as a keyboard, a pointing device, a scanner, or a networking device such as a switch or router, e.g., through a network adapter.

The computing device 500 may be implemented in a number of different forms, as shown in the figure. For example, it may be implemented as a standard server 520, or multiple times in a group of such servers. It may also be implemented as part of a rack server system 524. In addition, it may be implemented in a personal computer such as a laptop computer 522. Alternatively, components from computing device 500 may be combined with other components in a mobile device (not shown), such as device 550. Each of such devices may contain one or more of computing device 500, 550, and an entire system may be made up of multiple computing devices 500, 550 communicating with each other.

Computing device 550 includes a processor 552, memory 564, an input/output device such as a display 554, a communication interface 566, and a transceiver 568, among other components. The device 550 may also be provided with a storage device, such as a microdrive or other device, to provide additional storage. Each of the components 550, 552, 564, 554, 566, and 568, are interconnected using various buses, and several of the components may be mounted on a common motherboard or in other manners as appropriate.

The processor 552 can process instructions for execution within the computing device 550, including instructions stored in the memory 564. The processor may also include separate analog and digital processors. The processor may provide, for example, for coordination of the other components of the device 550, such as control of user interfaces, applications run by device 550, and wireless communication by device 550.

Processor 552 may communicate with a user through control interface 558 and display interface 556 coupled to a display 554. The display 554 may be, for example, a TFT LCD display or an OLED display, or other appropriate display technology. The display interface 556 may include appropriate circuitry for driving the display 554 to present graphical and other information to a user. The control interface 558 may receive commands from a user and convert them for submission to the processor 552. In addition, an external interface 562 may be provided in communication with processor 552, so as to enable near area communication of device 550 with other devices. External interface 562 may provide, for example, for wired communication, e.g., via a docking procedure, or for wireless communication, e.g., via Bluetooth or other such technologies.

The memory 564 stores information within the computing device 550. In one implementation, the memory 564 is a computer-readable medium. In one implementation, the memory 564 is a volatile memory unit or units. In another implementation, the memory 564 is a non-volatile memory unit or units. Expansion memory 574 may also be provided and connected to device 550 through expansion interface 572, which may include, for example, a SIMM card interface. Such expansion memory 574 may provide extra storage space for device 550, or may also store applications or other information for device 550. Specifically, expansion memory 574 may include instructions to carry out or supplement the processes described above, and may include secure information also. Thus, for example, expansion memory 574 may be provided as a security module for device 550, and may be programmed with instructions that permit secure use of device 550. In addition, secure applications may be provided via the SIMM cards, along with additional information, such as placing identifying information on the SIMM card in a non-hackable manner.

The memory may include for example, flash memory and/or MRAM memory, as discussed below. In one implementation, a computer program product is tangibly embodied in an information carrier. The computer program product contains instructions that, when executed, perform one or more methods, such as those described above. The information carrier is a computer- or machine-readable medium, such as the memory 564, expansion memory 574, or memory on processor 552.

Device 550 may communicate wirelessly through communication interface 566, which may include digital signal processing circuitry where necessary. Communication interface 566 may provide for communications under various modes or protocols, such as GSM voice calls, SMS, EMS, or MMS messaging, CDMA, TDMA, PDC, WCDMA, CDMA2000, or GPRS, among others. Such communication may occur, for example, through radio-frequency transceiver 568. In addition, short-range communication may occur, such as using a Bluetooth, WiFi, or other such transceiver (not shown). In addition, GPS receiver module 570 may provide additional wireless data to device 550, which may be used as appropriate by applications running on device 550.

Device 550 may also communicate audibly using audio codec 560, which may receive spoken information from a user and convert it to usable digital information. Audio codec 560 may likewise generate audible sound for a user, such as through a speaker, e.g., in a handset of device 550. Such sound may include sound from voice telephone calls, may include recorded sound, e.g., voice messages, music files, etc., and may also include sound generated by applications operating on device 550.

The computing device 550 may be implemented in a number of different forms, as shown in the figure. For example, it may be implemented as a cellular telephone 580. It may also be implemented as part of a smartphone 582, personal digital assistant, or other similar mobile device.

Various implementations of the systems and techniques described here can be realized in digital electronic circuitry, integrated circuitry, specially designed ASICs, computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs, also known as programs, software, software applications or code, include machine instructions for a programmable processor, and can be implemented in a high-level procedural and/or object-oriented programming language, and/or in assembly/machine language. As used herein, the terms "machine-readable medium" "computer-readable medium" refers to any computer program product, apparatus and/or device, e.g., magnetic discs, optical disks, memory, Programmable Logic Devices (PLDs) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the systems and techniques described here can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

The systems and techniques described here can be implemented in a computing system that includes a back-end component, e.g., as a data server, or that includes a middleware component such as an application server, or that includes a front-end component such as a client computer having a graphical user interface or a Web browser through which a user can interact with an implementation of the systems and techniques described here, or any combination of such back-end, middleware, or front-end components. The components of the system can be interconnected by any form or medium of digital data communication such as, a communication network. Examples of communication networks include a local area network ("LAN"), a wide area network ("WAN"), and the Internet.

The computing system can include clients and servers. A client and server are generally remote from each other and typically interact through a communication network. The relationship of client and server arises by virtue of computer programs running on the respective computers and having a client-server relationship to each other.

In addition, certain data may be treated in one or more ways before it is stored or used, so that personally identifiable information is removed. For example, in some embodiments, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over what information is collected about the user, how that information is used, and what information is provided to the user.

A number of embodiments have been described. Nevertheless, it will be understood that various modifications may be made without departing from the spirit and scope of the invention. Accordingly, other embodiments are within the scope of the following claims. While this specification contains many specific implementation details, these should not be construed as limitations on the scope of what may be claimed, but rather as descriptions of features that may be specific to particular embodiments. Certain features that are described in this specification in the context of separate embodiments can also be implemented in combination in a single embodiment.

Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, some processes depicted in the accompanying figures do not necessarily require the particular order shown, or sequential order, to achieve desirable results.

What is claimed is:

1. A computer system-implemented method comprising:
   receiving, by one or more processors of a machine learning system, data associated with multiple entities, wherein each entity is associated with an activity of a previous clinical trial program and the data comprises, for each entity, prior attributes for the associated activity of the previous clinical trial program;
   for each entity:
      determining, by the one or more processors of the machine learning system, a first future attribute and a second future attribute by providing the received data comprising the prior attributes to the machine learning system, the first future attribute indicating performance associated with the entity performing one or more activities for a future clinical trial program and
      the second future attribute indicating protocol compliance associated with the entity performing the one or more activities for the future clinical trial program;
      generating, by the one or more processors of the machine learning system, a weight value for each of the first future attribute and the second future attribute of the entity, the weight value reflecting prior performance and participation in previous clinical trial programs that include similar attributes as the first and second future attributes of the future clinical trial program;
   ranking, by the one or more processors of the machine learning system, each entity of the multiple entities for performing the one or more activities in the future clinical trial program, the ranking performed based on a tier indicator that corresponds to one or both of the weighted first future attribute or the weighted future second attribute for the entity;
   generating, by the one or more processors of the machine learning system, a data structure that comprises data indicative of the ranked entities for performing the one or more activities in the future clinical trial program; and selecting, by the one or more processors, one or more entities from the data structure to perform the one or more activities in the future clinical trial program.

2. The computer system-implemented method of claim 1, wherein each entity comprises at least one of (i) an investigator that is associated with a program, or (ii) a geographic location for a site adapted to host individuals that perform activities of the program.

3. The computer system-implemented method of claim 1, wherein the data associated with the multiple entities comprises:
   an entity's performance attributes in one or more previous clinical trial programs;
   an entity's participation in one or more previous clinical trial programs; and
   medical data indicative of participants previously enrolled in a clinical trial program associated with the entity.

4. The computer system-implemented method of claim 3, wherein determining the first future attribute that indicates the performance associated with the entity performing the one or more activities for the future clinical trial program comprises:
   analyzing historical performance data in the received data by:
      filtering the historical performance data in the received data for an entity's performance attributes in the past clinical trial programs; and
      determining a delivery attribute based on the filtered historical performance data, the delivery attribute indicating one or both of (i) the performance associated with the entity performing the one or more activities for the future clinical trial program or (ii) an appropriateness for the entity to participate in the one or more activities.

5. The computer system-implemented method of claim 4, wherein the delivery attribute ranges between a first value, a second value, and a third value, the first value indicating the entity is predicted to exceed performance expectations when conducting a program, the second value indicating the entity is predicted to not exceed minimum performance expectations when conducting a program, and the third value indicating the entity is appropriate for the program and no historical performance data is available for the entity, wherein the first value is less than the second value and the second value is less than the third value.

6. The computer system-implemented method of claim 1, wherein determining the second future attribute that indicates the protocol compliance associated with the entity for the future clinical trial program comprises:
   analyzing historical results data in the received data by:
      identifying deviations in a prior trial program associated with the entity, the deviations comprising one or more of (i) site-level deviations, (ii) a number of subjects having subject-level deviations, and (iii) protocol deviations across certain trial program sites; and
   determining a quality attribute based on the identified deviations in the prior trial program, the quality attribute indicating a likelihood of the entity to deviate from protocols of a subsequent program.

7. The computer system-implemented method of claim 1, wherein the weight value for the first attribute comprises at least one of:
   i) a weight value for respective performance factors included in analyzed performance data for the entity, where the respective performance factors are each relevant to determining the first future attribute of the entity; or
   ii) a weight value for respective participation factors included in the received data relating to the first future attribute of the entity, where the respective participation factors are each relevant to assessing the performance associated with the entity performing the one or more activities for the future clinical trial program.

8. The computer system-implemented method of claim 1, wherein generating the weight value for the second attribute further comprises:
   analyzing quality data used to determine the second future attribute and generating the weight value for the second future attribute based in part on the analyzed quality data, the second future attribute being a quality attribute,
   wherein the weight values include a weight value for respective quality factors included in the analyzed quality data, and where the respective quality factors are each relevant to assessing the protocol compliance associated with the entity for the future clinical trial program.

9. The computer system-implemented method of claim 1, wherein the machine learning system comprises one or more neural networks.

10. The computer system-implemented method of claim 1, wherein determining the first future attribute that indicates the performance associated with the entity performing the one or more activities for the future clinical trial program further comprises determining, by the machine learning system and based on analysis of the data, a scoring parameter that rates the performance associated with the entity performing the one or more activities for the future clinical trial program.

11. The computer system-implemented method of claim 1, wherein determining the second future attribute that indicates the protocol compliance associated with the entity for the future clinical trial program further comprises determining, by the machine learning system and based on analysis of the data, a scoring parameter that rates the protocol compliance associated with the entity for the future clinical trial program.

12. A system, comprising:
   one or more processing devices; and
   one or more non-transitory machine-readable storage devices storing instructions that are executable by the one or more processing devices to cause performance of operations comprising:
      receiving, by one or more processors of a machine learning system, data associated with multiple entities, wherein each entity is associated with an activity of a previous clinical trial program and the data comprises, for each entity, prior attributes for the associated activity of the previous clinical trial program;
      for each entity:
         determining, by the one or more processors of the machine learning system, a first future attribute and a second future attribute by providing the received data comprising the prior attributes to the machine learning system, the first future attribute indicating performance associated with the entity performing one or more activities for a future clinical trial program and the second future attribute indicating protocol compliance associated with the entity performing the one or more activities for the future clinical trial program;

generating, by the one or more processors of the machine learning system, a weight value for each of the first future attribute and the second future attribute of the entity, the weight value reflecting prior performance and participation in previous clinical trial programs that include similar attributes as the first and second future attributes of the future clinical trial program;

ranking, by the one or more processors of the machine learning system, each entity of the multiple entities for performing the one or more activities in the future clinical trial program, the ranking performed based on a tier indicator that corresponds to one or both of the weighted first future attribute or the weighted future second attribute for the entity;

generating, by the one or more processors of the machine learning system, a data structure that comprises data indicative of the ranked entities for performing the one or more activities in the future clinical trial program; and selecting, by the one or more processors, one or more entities from the data structure to perform the one or more activities in the future clinical trial program.

13. The system of claim 12, wherein each entity comprises at least one of (i) an investigator that is associated with a program, or (ii) a geographic location for a site adapted to host individuals that perform activities of the program.

14. The system of claim 12, wherein the data associated with the multiple entities comprises:
an entity's performance attributes in one or more previous clinical trial programs;
an entity's participation in one or more previous clinical trial programs; and
medical data indicative of participants previously enrolled in a clinical trial program associated with the entity.

15. The system of claim 14, wherein determining the first future attribute that indicates the performance associated with the entity performing the one or more activities for the future clinical trial program comprises:
analyzing historical performance data in the received data by:
filtering the historical performance data in the received data for an entity's performance attributes in the past clinical trial programs; and
determining a delivery attribute based on the filtered historical performance data, the delivery attribute indicating one or both of (i) the performance associated with the entity performing the one or more activities for the future clinical trial program or (ii) an appropriateness for the entity to participate in the one or more activities.

16. The system of claim 15, wherein the delivery attribute ranges between a first value, a second value, and a third value, the first value indicating the entity is predicted to exceed performance expectations when conducting a program, the second value indicating the entity is predicted to not exceed minimum performance expectations when conducting a program, and the third value indicating the entity is appropriate for the program and no historical performance data is available for the entity, wherein the first value is less than the second value and the second value is less than the third value.

17. The system of claim 12, wherein determining the second future attribute that indicates the protocol compliance associated with the entity for the future clinical trial program comprises:
analyzing historical results data in the received data by:
identifying deviations in a prior trial program associated with the entity, the deviations comprising one or more of (i) site-level deviations, (ii) a number of subjects having subject-level deviations, and (iii) protocol deviations across certain trial program sites; and
determining a quality attribute based on the identified deviations in the prior trial program, the quality attribute indicating a likelihood of the entity to deviate from protocols of a subsequent program.

18. The system of claim 12, wherein the weight value for the first attribute comprises at least one of:
i) a weight value for respective performance factors included in analyzed performance data for the entity, where the respective performance factors are each relevant to determining the first future attribute of the entity; or
ii) a weight value for respective participation factors included in the received data relating to the first future attribute of the entity, where the respective participation factors are each relevant to assessing the performance associated with the entity performing the one or more activities for the future clinical trial program.

19. The system of claim 12, wherein generating the weight value for the second attribute further comprises:
analyzing quality data used to determine the second future attribute and generating the weight value for the second future attribute based in part on the analyzed quality data, the second future attribute being a quality attribute,
wherein the weight values include a weight value for respective quality factors included in the analyzed quality data, and where the respective quality factors are each relevant to assessing the protocol compliance associated with the entity for the future clinical trial program.

20. A non-transitory computer-readable medium storing software comprising instructions executable by one or more computers which, upon such execution, cause the one or more computers to perform operations comprising:
receiving, by one or more processors of a machine learning system, data associated with multiple entities, wherein each entity is associated with an activity of a previous clinical trial program and the data comprises, for each entity, prior attributes for the associated activity of the previous clinical trial program;
for each entity:
determining, by the one or more processors of the machine learning system, a first future attribute and a second future attribute by providing the received data comprising the prior attributes to the machine learning system, the first future attribute indicating performance associated with the entity performing one or more activities for a future clinical trial program and
the second future attribute indicating protocol compliance associated with the entity performing the one or more activities for the future clinical trial program;
generating, by the one or more processors of the machine learning system, a weight value for each of the first future attribute and the second future attribute of the entity, the weight value reflecting prior performance and participation in previous clinical trial programs that include similar attributes as the first and second future attributes of the future clinical trial program;

ranking, by the one or more processors of the machine learning system, each entity of the multiple entities for performing the one or more activities in the future clinical trial program, the ranking performed based on a tier indicator that corresponds to one or both of the weighted first future attribute or the weighted future second attribute for the entity;

generating, by the one or more processors of the machine learning system, a data structure that comprises data indicative of the ranked entities for performing the one or more activities in the future clinical trial program; and selecting, by the one or more processors, one or more entities from the data structure to perform the one or more activities in the future clinical trial program.

21. The non-transitory computer-readable medium of claim 20, wherein each entity comprises at least one of (i) an investigator that is associated with a program, or (ii) a geographic location for a site adapted to host individuals that perform activities of the program.

22. The non-transitory computer-readable medium of claim 20, wherein the data associated with the multiple entities comprises:

an entity's performance attributes in one or more previous clinical trial programs;

an entity's participation in one or more previous clinical trial programs; and medical data indicative of participants previously enrolled in a clinical trial program associated with the entity.

23. The non-transitory computer-readable medium of claim 22, wherein determining the first future attribute that indicates the performance associated with the entity performing the one or more activities for the future clinical trial program comprises:

analyzing historical performance data in the received data by:
 filtering the historical performance data in the received data for an entity's performance attributes in the past clinical trial programs; and determining a delivery attribute based on the filtered historical performance data, the delivery attribute indicating one or both of (i) the performance associated with the entity performing the one or more activities for the future clinical trial program or (ii) an appropriateness for the entity to participate in the one or more activities.

* * * * *